United States Patent [19]

Bell et al.

[11] Patent Number: 4,643,173

[45] Date of Patent: Feb. 17, 1987

[54] HEATED TRACTION BELT

[76] Inventors: John H. Bell; George Spector, both of 233 Broadway RM 3615, New York, N.Y. 10007

[21] Appl. No.: 696,256

[22] Filed: Jan. 29, 1985

[51] Int. Cl.$^4$ .................................................. A61F 5/01

[52] U.S. Cl. .................................. 128/68.1; 128/82.1

[58] Field of Search ..................... 128/24.1, 68.1, 82.1

[56] References Cited

U.S. PATENT DOCUMENTS

| | | | |
|---|---|---|---|
| 1,234,700 | 7/1917 | McLain | 128/24.1 |
| 2,638,091 | 5/1953 | Varco | 128/24.1 |
| 3,075,517 | 1/1963 | Morehead | 128/24.1 |
| 3,323,517 | 6/1967 | Keller | 128/24.1 |

FOREIGN PATENT DOCUMENTS

| | | | |
|---|---|---|---|
| 1491545 | 7/1969 | Fed. Rep. of Germany | 128/24.1 |
| 327608 | 6/1903 | France | 128/24.1 |

*Primary Examiner*—Edgar S. Burr
*Assistant Examiner*—Tonya Eckstine

[57] ABSTRACT

A heated traction belt usable by a user in traction on a bed and including a heater disposed internally in the rear portion of the belt and connected by a wire to a controller that is attached to the belt by VELCRO, VELCRO is also used to keep the belt closed when worn by the user, a heat control switch is disposed in the belt and connected to a weight strap so that when a weight is applied to the traction the weight strap pulls taunt and closes the heat control switch and operates the heater.

1 Claim, 5 Drawing Figures

HEATED TRACTION BELT

BACKGROUND OF THE INVENTION

The present invention relates to traction belts. More particularly, it relates to traction belts having accompanying heating devices.

Devices of the above-mentioned general type are known in the art. For example, U.S. Pat. No. 1,975,329 to MacSweeney teaches an electric heating pad with fasenting means to hold it in place while in use. This patent applies to heating pads in general and does not teach a combined traction belt-heating pad that forms an integral unit. Another example, U.S. Pat. No. 2,387,192 to Straits teaches a fracture apparatus whereby a splint is formed with a channel for holding a heated fluid. This patent applies to splints and not traction devices and additionally cannot assure constant heat. A final example, U.S. Pat. No. 3,176,684 to Walsh teaches a pelvic traction belt without any integrally connected heating means.

SUMMARY OF THE INVENTION

It is the primary object of the present invention to provide a heated traction belt that avoids the disadvantages of the prior art.

Another object of the present invention is to provide a heated traction belt that is an integral unit.

Still another object of the present invention is to provide a heated traction belt that is held in place on the user by VELCRO.

Yet another object of the present invention is to provide a heated traction belt that has provisions for removing the heating pad and controller.

Still yet another object of the present invention is to provide a heated traction belt that contains a heat control switch which is closed when the traction weight is applied to the weight strap which is attached to the belt.

BRIEF DESCRIPTION OF THE DRAWINGS

The Figures thereon are briefly described in the following manner:

FIG. 3 is a cross sectional view taken along line 3—3 in FIG. 2 showing the internal structure of the belt with heater built in.

DETAILED DESCRIPTION OF THE PREFERRED EMBODIMENTS

Figure 1:
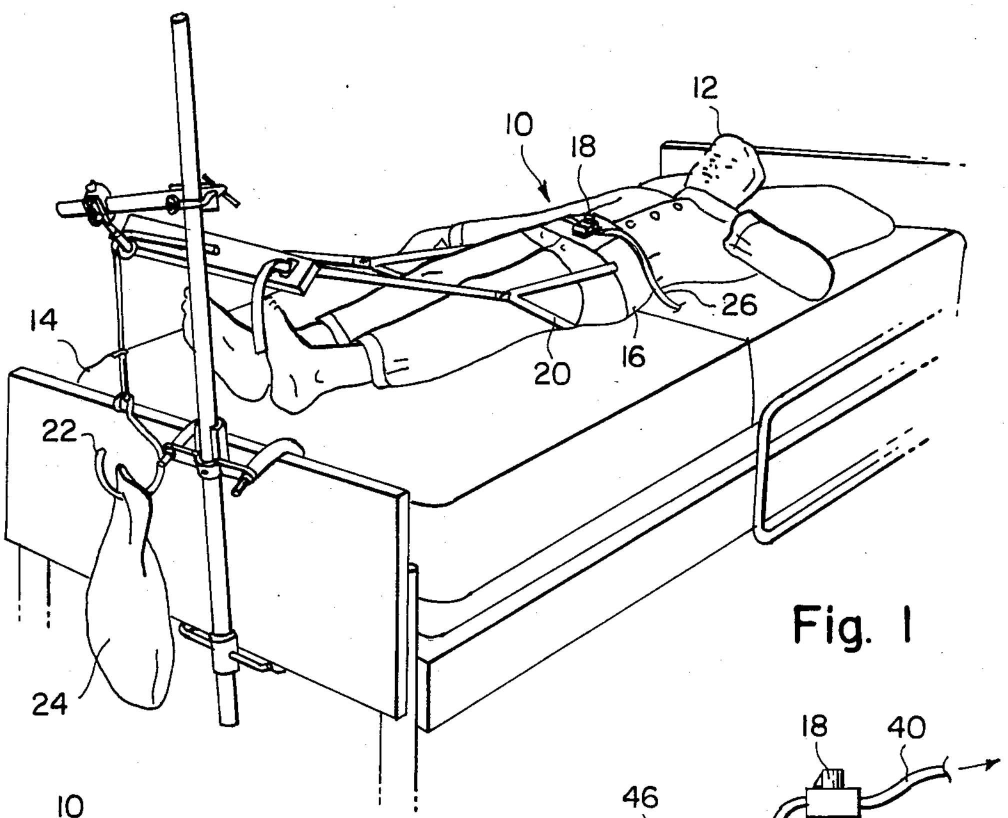
FIG. 1 is a perspective view of a patient lying on a hospital bed using the Invention.
Figure 2:
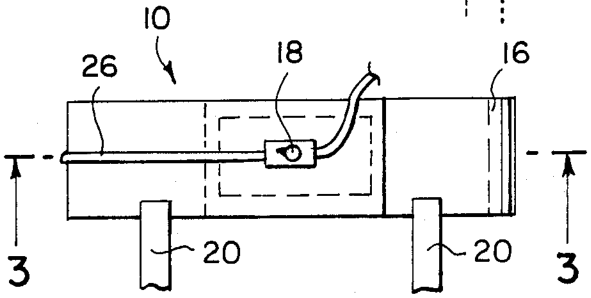
FIG. 2 is a top view of the belt closed with parts broken away.

Referring now to FIGS. 1 and 2, the heated traction belt of the present invention is shown generally at 10 in use on a person 12 lying in a traction bed 14. The traction belt 10 has a belt 16 with a control 18 mounted thereon. Connected to the belt 16 are weight straps 20 which are connected via a weight hook 22 to a weight 24 for applying traction. The control 18 is connected to a wire 26. The traction belt 10 is worn on the waist of the person 12 and the weight straps 20 extend in the direction of the legs of the user 12.

Figure 3:
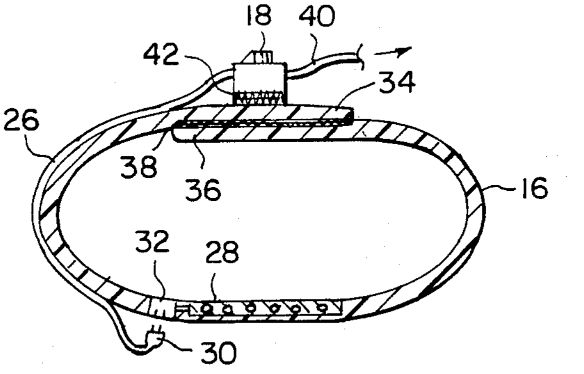

A heater 28, as shown in FIG. 3, is built internally into the rear portion of the belt 16 and is controlled by the control 18 disposed on the front portion of the belt 16. The wire 26 of the control 18 has a plug 30 at its free end which mates with a socket 32 which is internally connected to the heater 28. The free ends 34 and 36 of the belt 16 are held together, in the closed position, by VELCRO 38. Another wire 40, connected to the control 18, is plugged into an outlet to supply power to the heater 28. The control 18 is attached to the belt 16 by VELCRO 42.

Figure 4:
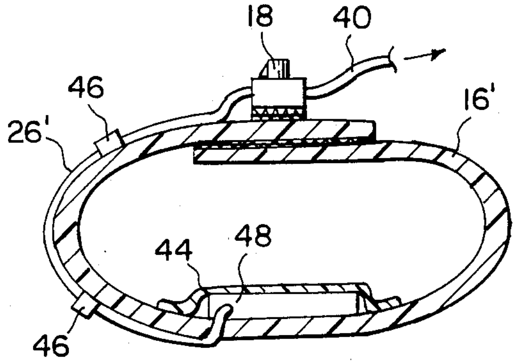
FIG. 4 is a cross sectional view similar to FIG. 3 of a first modification showing a pocket in rear portion of the belt to hold a standard heating pad within.

FIG. 4, shows an alternate embodiment of the present invention in which the heater is not an internal part of the belt 16' but is rather fittable into a thin nylon pocket 44 disposed externally on the rear section of the belt 16'. The wire 26' is connected to the control 18 and is held to the belt 16' by retainer clips 46. The free end 48 of the wire 26' remains in the pocket 44 and attaches to the heating pad when it is inserted.

Figure 5:
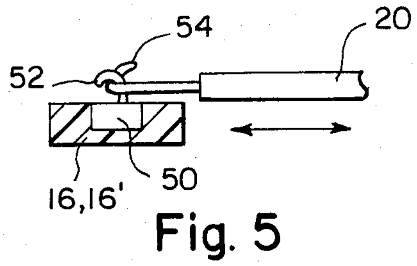
FIG. 5 is a cross sectional view of a second modification showing a heat control switch built into the belt and activated by the weight strap.

The heater of the traction belt may be turned on automatically when the weight 24 pulls the weight straps 20, as is shown in FIG. 5. A heat control switch 50 is built into the traction belt in the area of the weight straps 20. The control switch 50 is formed with a hook 52 which mates with a hook 54 disposed on an end of the weight straps 20. When the weight 24 is applied, the weight strap 20 becomes taunt and due to the hooks 52 and 54 causes the heat control switch to move, close and start the heater.

We claim:

1. A heated traction belt for a user comprising:
   - a belt;
   - heating means mounted in said belt;
   - means for activating said heating means; and
   - a front closure for holding said belt on the user, said heating means being a heater disposed internally in the rear portion of said belt connected by a wire to a controller that is attached to said front closure, said activating means including a heat control switch disposed on said belt and connected to a weight strap so that when a weight is applied to said weight strap the weight strap pulls taut and closes the heat control switch and operates said heater.

* * * * *